United States Patent [19]

Baird et al.

[11] Patent Number: 5,262,323
[45] Date of Patent: Nov. 16, 1993

[54] BACTERIAL STRAIN

[75] Inventors: Sheila Baird, Berkshire; Susan Ely, Bucks; Graham M. Gibb, Farnborough; Janet M. Tippett, Berkshire, all of England

[73] Assignee: Imperial Chemical Industries PLC, London, England

[21] Appl. No.: 784,181

[22] Filed: Oct. 31, 1991

[30] Foreign Application Priority Data

Nov. 1, 1990 [GB] United Kingdom ............... 9023735

[51] Int. Cl.$^5$ .................. C12N 1/20; A01N 63/00; A61K 37/00
[52] U.S. Cl. ................... 435/252.5; 435/832; 435/252.31; 424/93 L
[58] Field of Search ............ 435/252.31, 252.3, 832, 435/91, 252.5; 514/2; 424/93 A, 93 L

[56] References Cited

U.S. PATENT DOCUMENTS

| | | | |
|---|---|---|---|
| 4,764,372 | 8/1988 | Herrnstadt et al. | 435/832 |
| 4,766,203 | 8/1988 | Krieg et al. | 435/832 |
| 4,771,131 | 9/1988 | Herrnstadt et al. | 435/91 |
| 4,797,276 | 1/1989 | Herrnstadt et al. | 435/832 |
| 4,853,331 | 8/1989 | Herrnstadt et al. | 435/252.3 |
| 4,865,981 | 9/1989 | Herrnstadt et al. | 435/252.31 |
| 4,910,136 | 3/1990 | Herrnstadt et al. | 435/252.3 |
| 4,935,236 | 6/1990 | Herrnstadt et al. | 514/2 |
| 5,002,765 | 3/1991 | Herrnstadt et al. | 424/93 A |
| 5,017,373 | 5/1991 | Herrnstadt et al. | 424/93 A |
| 5,120,536 | 6/1992 | Cidaria et al. | 435/252.5 |
| 5,208,017 | 5/1993 | Bradfisch et al. | 424/93 L |

FOREIGN PATENT DOCUMENTS 9116433 10/1991 PCT Int'l Appl. .

OTHER PUBLICATIONS

Rupar, M. J., et al., "Applied and Environmental Microbiology," vol. 57(11), Nov. 1991, pp. 3337–3344.

*Primary Examiner*—Douglas W. Robinson
*Assistant Examiner*—Kristin K. Larson
*Attorney, Agent, or Firm*—Cushman, Darby & Cushman

[57] ABSTRACT

The novel strain JHCC 4279 of *Bacillus thuringiensis* and insecticidal compositions containing insecticidal protein endotoxin produced by the strain JHCC 4279 which protects plants from Diabrotica by exposing larvae to the insecticidal protein endotoxin produced by the strain. Novel genes for insecticidal proteins may be isolated from strain JHCC 4279.

1 Claim, No Drawings

BACTERIAL STRAIN

The present invention relates to a novel bacterial strain, and in particular to a novel strain of the bacterium *Bacillus thuringiensis* and uses therefor.

The organism *Bacillus thuringiensis* produces a crystal-associated protein endotoxin which kills insect larvae upon ingestion. It is not however toxic to mammals. It is thus very useful as an agricultural insecticide, in particular against Lepidoptera, Coleoptera and Diptera. Strains of *Bacillus thuringiensis* have been used as agricultural insecticides for a number of decades.

The most extensively characterized strain of *Bacillus thuringiensis* active against coleopteran pests is *Bacillus thuringiensis* subsp. tenebrionis, as deposited in the German Collection of Microorganisms (Deutsche Sammlung von Microorganismen) under the reference DSM 2803. We have now discovered a novel strain of *Bacillus thuringiensis* having some properties similar to *Bacillus thuringiensis* subsp. tenebrionis, but distinguished therefrom by specific insecticidal activity against coleopteran larvae of the genus Diabrotica.

According to the present invention we provide the novel strain JHCC 4279 of *Bacillus thuringiensis*, deposited on 25 Jan. 1990 at the National Collections of Industrial and Marine Bacteria, Scotland, under the accession number NCIB 40252. We further provide a novel insecticidal composition characterized in that it contains an insecticidal protein endotoxin produced by said strain JHCC 4279, and a method of protecting plants from insect attack which comprises exposing the insect larvae to insecticidal protein endotoxin produced by the said strain JHCC 4279. We further provide novel insecticidal protein genes capable of isolation from said strain JHCC 4279.

*B. thuringiensis* strain JHCC 4279 was a soil isolate from Polk County, Iowa, USA. In colonial morphology, strain JHCC 4279 is generally similar to other strains of *Bacillus thuringiensis* although the crystalline inclusions are markedly less prominent than are those of other strains. For this reason it could be argued that the strain should be classified as *Bacillus cereus*. However, this is a question solely of scientific terminology and is irrelevant to the the questions of how to make and how to use the present invention.

The biochemical properties of strain JHCC 4279 are generally similar to those of other *Bacillus thuringiensis* strains. The biochemical properties of *Bacillus thuringiensis* strain JHCC 4279 are shown in detail in Table 1, and compared with those of the known strains HD-1 and DSM 2803.

In view of these biochemical similarities, it is surprising that the gene or genes encoding insecticidal protein(s) in strain JHCC 4279 show, as judged by DNA hybridization analysis, very little DNA sequence homology to the *Bacillus thuringiensis* subsp. tenebrionis endotoxin gene or to the novel endotoxin gene described in PCT Patent Application WO 90/00706 (filed 8 May 1990) and also shown to be active against Diabrotica. Use of the coding sequence of the subsp. tenebrionis endotoxin gene or the novel endotoxin gene as DNA probes is not sufficient to generate a signal from coding sequences for the insecticidal protein gene(s) in strain JHCC 4279.

The newly discovered *Bacillus thuringiensis* strain 4279 shows a significantly improved specificity of insecticidal activity as compared with DSM 2803. In particular, strain JHCC 4279 shows a more selective activity against beetles than do other known coleopteran-active *B. thuringiensis* strains in that it is specifically larvacidal to Diabrotica spp.

The strain according to the invention may be prepared in any quantity required by fermenting a sample of NCIB 40252 obtained from the National Collections of Industrial and Marine Bacteria under suitable conditions in an appropriate medium. Such conditions and media are well known to the art. The media will, for example, generally contain a nitrogen source (e.g. fish protein) and a carbohydrate source such as starch. Suitable conditions include a temperature in the range of 15°–30° C., and an appropriately neutral pH. Fermentation may be conveniently carried out in batches, typically for periods of 3–5 days (until complete sporulation is observed, but prior to lysis).

Insecticidal compositions according to the invention may be obtained from the fermentation liquor by concentration, for example by centrifugation or filtration followed by addition of any desired and appropriate formulating agents. Formulating agents which may be useful include for example surface active agents (e.g. wetting agents), solid diluents, dispersing agents and UV stabilisers. If desired, solid formulations may be prepared by known methods.

The process of the invention is generally carried out by treating (e.g. spraying) plants infested or liable to infestation by insects with insecticidal compositions as described above diluted with a diluent such as water. The effective agent is insecticidal protein; if desired this may be applied to the plants, independently of the sporulated bacterial culture that produced it. Separation of the protein from the bacterial lysate is however generally not necessary.

One method of carrying out the process of the invention is to arrange for the plant susceptible to insect attack to produce the insecticidal protein in situ. This is done by cloning an insecticidal protein gene from strain NCIB 40252, as indicated below, providing it with a suitable promoter (for example the CaMV35S promoter) which will cause expression of the gene in plants, and transforming the plant by known methods (e.g. bombardment of maize suspension cells with DNA-coated particles).

One method for cloning an insecticidal protein gene for which there is no DNA probe is by "reverse-cloning". This involves purifying the insecticidally-active protein to homogeneity, followed by N-terminal amino acid sequence determination of the pure protein so obtained. The amino acid sequence information is then used to design a degenerate oligonucleotide DNA probe for use in screening a genomic library prepared from *B. thuringiensis* strain 4279, and cloning the relevant gene by known means.

Larvae which are combated by the process of the invention may include Diabrotica spp., for example those shown in Table 2 below.

The process of the invention may be used to protect a wide variety of plants prone to infestation by Diabrotica. Specific examples of commercially-important plants to be protected by the invention are maize (corn), potato, tomato, cotton, tobacco and cucurbits.

The following Examples illustrate the invention.

EXAMPLE 1

Isolation of the *B. thuringiensis* strain JHCC 4279 according to the invention.

Soil samples were diluted by placing 5.0 g of the sample into 45 ml of 0.5% peptone to give a $10^{-1}$ dilution prior to emulsification. The sample was then heated to 60° C. for 10 minutes in a water bath. Sequential dilutions were then made prior to plating 0.1 ml of the $10^{-3}$ and $10^{-5}$ dilutions onto B. cereus selective agar plates (Bacillus cereus agar base, Oxoid) and esculin agar plates (in g/liter of $H_2O$: esculin 1.0; ferric citrate 0.5; peptone 10; NaCl 5; Oxoid agar 10). The plated samples were incubated at 30° C. for 5 days. Slides were made of potential B. thuringiensis colonies, stained according to Smirnoff's procedure and examined microscopically at 1000X magnification for the presence of stained, parasporal crystals.

Crystal-positive colonies were streaked onto L agar (10 g tryptone, 10 g yeast extract, 5 g NaCl, 10 g agar per liter) in order to ensure a pure culture, and incubated at 30° C. Purified colonies were incubated overnight in L broth; after incubation an equal volume of 80% sterile glycerol was added prior to storage at $-70°$ C.

EXAMPLE 2

Propagation of the B. thuringiensis strain JHCC 4279 on CRL 1 solid media.

Inoculum was transferred from a glycerol storage vial onto an L agar plate to check for purity. A representative sweep of colonies was then used to inoculate 5 ml of L broth (10 g tryptone, 10 g yeast extract, 5 g NaCl per liter) prior to incubation with shaking at 30° C. for 3-5 hours. One milliliter of this culture was then used to inoculate a preparative (210 mm×210 mm) Petri plate containing 300 ml of CRL 1 medium agar (in g or ml/liter of water: nutrient broth 8; glucose 6; yeast extract 5; xylose 0.5; cotton seed flour extract 30 ml; corn steep liquor 3.2 ml; Mary Mendel's salt mixture 1 ml; Oxoid agar 15). Mary Mendel's salt mixture is:

| Mary Mendel's Salts | |
|---|---|
| Distilled Water | 495 ml |
| HCl conc. | 5 ml |
| $FeSO_4$ | 2.5 g |
| $MnSO_4, H_2O$ or $MnCl_2.4H_2O$ | 0.98 g |
| $ZnCl_2$ or $ZnSO_4.4H_2O$ | 1.76 g |

Cultures were incubated for 5 days at 30° C. The cells, spores and crystals were then harvested by scraping confluent growth from the agar surface prior to freeze-drying.

EXAMPLE 3

Propagation of the B. thuringiensis strain JHCC 4279 in CRL 1 liquid culture according to the invention.

Inoculum was transferred from a glycerol storage vial to a 250 ml Erylenmeyer flask containing 100 ml of CRL 1 medium (in g or ml/liter of water: nutrient broth 8; glucose 6; yeast extract 5; xylose 0.5; cotton seed flour extract 30 ml; corn steep liquor 3.2 ml; Mary Mendel's salt mixture 1 ml) and incubated with agitation at 30° C. and 3400 rpm. After 24 hours, the entire 100 ml was used to inoculate 1 liter of the same medium in a 2L flask; this was incubated with agitation for 5 days at 30° C. The cells, spores and crystals were then harvested by centrifugation and acetone precipitated using the Dulmage method.

EXAMPLE 4

Large Scale fermentation of B. thuringiensis strain JHCC 4279 in TSB medium according to the invention.

Inoculum was transferred from a glycerol storage rail to an L-agar plate.

After overnight incubation at 30° C. an inoculum was transferred from the plate to a baffle flask containing 200 ml Nutrient Broth (Oxoid) prior to incubation with shaking for 10 h at 28° C. The inoculum was transferred to a Braun BioStat E fermenter containing 13 liters of double-strength (2x) Tryptone Soya Broth (Oxoid) supplemented with 20 g/liter glucose monohydrate and prewarmed to 30° C. Fermentation was allowed to proceed at 30° C. pH7.00±0.02, stirring at 800 rpm, with a dissolved oxygen ($PO_2$) setting of 70. PPG 2025 antifoam (BDH) was used at a 3:90 setting. The developmental stage of the culture was monitored every 3 hours prior to harvest at 90-100% sporulation. [N.B. Harvest occurs before sporulated cells have lysed]. Harvested cells were collected by centrifugation and washed twice in cold, sterile distilled $H_2O$ prior to lyophilization. 10 g aliquots of lyophilized fermentation product were stored in sterile containers at $-70°$ C.

EXAMPLE 5

Formulation according to the invention.

Upon completion of the fermentation JHCC 4279 bacteria can be harvested by first separating the B. thuringiensis spores and crystals from the fermentation broth as described in Example 2. The recovered spores and crystals can be resuspended in 100 ml of water and formulated into a liquid concentrate by adding 4.9 g of Morwet D-425 (dispersing agent), 4.9 g of Veegum HV (suspending agent), 4.9 ml of Tween 80 (wetting agent) and 24.4 ml of Sorbo (anti-freezing agent). Each ingredient is added separately in the order stated above. The product is kept at 4° C. prior to use.

EXAMPLE 6

Partial purification of insecticidal protein(s) from B. thuringiensis strain 4279.

10 g of lyophilized, sporulated culture prepared as described in Example 4 was suspended in 100 ml 0.1M 3-cyclohexylamino-1-propanesulfonic acid (CAPS) buffer pH 10.5 and hand-homogenized at 4° C. prior to sonic disruption at room temperature. The sample was incubated for 2 hours at 37° C. prior to centrifugation at 100,000 g for 1 hour at 4° C. The resultant supernatant was dialyzed into 10 mM Tris pH 8.0 prior to Mono Q preparative ion exchange chromatography. The insecticidal proteins were eluted from the column in the 0-200 mM region of the 0-400 mM NaCl elution gradient. Further purification was then achieved by an hydroxylapatite chromatographic step in which the insecticidal proteins did not bind to the column when loaded in 10 mM phosphate buffer pH 7.0. This protocol results in a purified sample consisting of 6-8 proteins ranging in size from 14-54 kilodaltons.

EXAMPLE 7

This Example illustrates the specificity of the insecticidal activity of B. thuringiensis strain JHCC 4279 as compared with other strains of B. thuringiensis.

Specificity of the larvicidal activity of B. thuringiensis strain JHCC 4279.

For each B. thuringiensis strain, a mixture of spores and crystals was prepared by incubating the organism at 30° C. for 5 days on 210 mm×210 mm Petri plates as in Example 2, scraping confluent growth from the agar surface and freeze-drying. For tests on first instar larvae of Western Corn Rootworm (*Diabrotica virgifera virgifera*), freeze-dried spores and crystals were mixed with sterile water and a sterile sucrose solution to give the treatment rates indicated in Table 3 in parts per million (ppm) and a final sucrose concentration of 2.5%. The solubilized spore/crystal (treatment) mixture was homogeneously dispersed by sonication in a water bath sonicator for 5 minutes. The treatment was then vortexed and applied as 0.075 ml of solution to a disk 1.5 cm in diameter cut from "Teri towels" (Kimberly Clark product #34770). One test consisted of 5-10 Teri towel disks with applied treatment, each held in a separate Falcon (TM) test dish prior to infestation with 5 first instar larvae per dish. Tests were placed in a closed Styrofoam (polystyrene) box with a moistened Teri towel placed in the bottom as an humidity source; the box was incubated in a constant-temperature room at 78°-80° F. for 5 days after treatment (DAT) prior to evaluation of the bioassay. The conditions inside the Styrofoam box were 74°-76° F. and 80% relative humidity. Tests were evaluated using a dissecting microscope.

For tests on 1-day-old Colorado Potato Beetle (*Leptinotarsa decemlineata*) larvae, freeze-dried spores and crystals were mixed with sterile water and presented on potato leaves dipped in this suspension.

For tests on first instar European Corn Borer (*Ostrinia nubilalis*), Corn Earworm (*Heliothis zea*) and Fall Armyworm (*Spodoptera frugiperda*) freeze-dried spores and crystals were mixed with an appropriate conventional artificial insect diet. A comparison of the activity spectrum of *B. thuringiensis* strain JHCC 4279 with those of a *B. thuringiensis* subsp. tenebrionis-like strain (JHCC 4580) and a *B. thuringiensis* subsp. kurstaki strain (JHCC 4360) is shown in Table 3, and illustrates the selective effect of strain JHCC 4279.

Example 8 illustrates the efficacy of *B. thuringiensis* strain JHCC 4279 on two Diabrotica spp.

EXAMPLE 8

Efficacy of *B. thuringiensis* strain JHCC 4279 against Western Corn Rootworm and Southern Corn Rootworm For each *B. thuringiensis* strain, a mixture of spores and crystals was prepared by incubating the organism at 30° C. for 5 days on 210 mm×210 mm Petri plates as in Example 2, scraping confluent growth from the agar surface and freeze-drying. Freeze-dried spores and crystals were mixed with sterile sucrose to give a final concentration of 2.5% sucrose for tests on first instar Western Corn Rootworm (*Diabrotica virgifera virgifera*) larvae and first instar Southern Corn Rootworm (*Diabrotica undecimpunctata howardi*). Tests were set up, incubated and evaluated as in Example 7. Results over a treatment rate range are presented in Table 4, and the subsp. tenebrionis-type strain JHCC 4580 is shown for comparison. In another test, single Falcon cups (5 larvae per cup) were used to test the efficacy of *B. thuringiensis* strain 4279, the *B. thuringiensis* subsp. tenebrionis strain (JHCC 4580) and a *B. thuringiensis* subsp. kurstaki strain (JHCC 4360). Results of these tests are shown in Table 5 and again illustrate the more selective effect of strain JHCC 4279. furthermore, the results in Tables 4 and 5 illustrate the efficacy of strain JHCC 4279 in the control of two Diabrotica spp.

Example 9 illustrates the reproducibility of the insecticidal properties of *B. thuringiensis* strain JHCC 4279 in the control of Western Corn Rootworm and a comparison with other strains of *B. thuringiensis*.

EXAMPLE 9

Efficacy and specificity of four separate preparations of *B. thuringiensis* strain JHCC 4279.

For each *B. thuringiensis* strain, four separate preps of spore/crystal mixture were prepared by incubating the organism at 30° C. for 5 days on 210 mm×210 mm Petri plates as in Example 2, scraping confluent growth from the agar surface and freeze-drying. Freeze-dried spores and crystals were mixed with sterile sucrose to give a final concentration of 2.5% sucrose for tests on first instar Western Corn Rootworm (*Diabrotica virgifera virgifera*) larvae. Tests were set up, incubated and evaluated as indicated in Example 7. Comparison of the activity of these separate preparations of *B. thuringiensis* strain JHCC 4279 with separate preparations of a *B. thuringiensis* subsp. tenebrionis strain (JHCC 4580) and a *B. thuringiensis* subsp. kurstaki strain (JHCC 4360) is shown in Table 6 for Corn Rootworm control, and illustrates the equivalent efficacy of strains JHCC 4279 and JHCC 4580 and the equivalence between separate preparations. These preparations were also presented as indicated in Example 7 in tests on the Lepidopteran pests, Corn Earworm and Fall Army Worm as shown in Table 7; these results together with those in Table 3 also indicate that strain JHCC 4279 is more selective in its insecticidal activity than are strains JHCC 4580 or JHCC 4360.

Example 10 illustrates the larvacidal activity of partially-purified protein samples from strain JHCC 4279.

EXAMPLE 10

Larvicidal activity of partially-purified protein samples from *B. thuringiensis* JHCC 4279 against Western Corn Rootworm.

In two separate experiments, partially-purified protein samples were prepared as described in Example 6. Western Corn Rootworm tests were set up, incubated and evaluated as in Example 7. Results of these tests are shown in Table 8 and indicate that partially-purified protein samples from strain JHCC 4279 are insecticidal to Western Corn Rootworm. Furthermore these data show that the purification procedure has resulted in an increase in larvicidal specific activity as judged by the efficacy of the purified sample at a concentration 10-fold less than that of the starting material, and the enhanced efficacy of the purified sample as compared with the unpurified CAPS extract.

TABLE 1

| Reagent | Biochemical Markers on Microtiter Plate | | |
|---|---|---|---|
| | HD-1 | DSM 2803 | JHCC 4279 |
| Glycerol | — | — | +/− |
| Erythritol | — | — | — |
| D-arabinose | — | — | — |
| L-arabinose | — | — | — |
| Ribose | + | +/− | + |
| D-xylose | — | — | — |
| L-xylose | — | — | — |
| Adonitol | — | — | — |
| β-methyl-xyloside | — | — | — |
| Galactose | — | — | — |
| D-glucose | + | + | + |
| D-fructose | + | + | + |
| D-mannose | — | + | + |
| L-sorbose | — | — | — |

TABLE 1-continued

Biochemical Markers on Microtiter Plate

| Reagent | HD-1 | DSM 2803 | JHCC 4279 |
|---|---|---|---|
| Rhamnose | − | − | − |
| Dulcitol | − | − | − |
| Inositol | − | − | − |
| Mannitol | − | − | − |
| Sorbitol | − | − | − |
| α-methyl-D-mannoside | − | − | − |
| α-methyl-D-glucoside | − | − | − |
| N acetyl glucosamine | + | + | + |
| Amygdaline | − | − | − |
| Arbutine | + | + | + |
| Esculine | + | +/− | + |
| Salicine | + | − | + |
| Cellobiose | + | − | +/− |
| Maltose | + | + | + |
| Lactose | − | − | − |
| Melibiose | − | − | − |
| Saccharose | − | + | − |
| Trehalose | + | + | + |
| Inuline | − | − | − |
| Melezitose | − | − | − |
| D-raffinose | − | − | − |
| Amidon | + | + | + |
| Glycogene | + | + | + |
| Xylitol | − | − | − |
| β-gentiobiose | − | − | − |
| D-turanose | − | − | − |
| D-lyxose | − | − | − |
| D-tagatose | − | − | − |
| D-fucose | − | − | − |
| L-fucose | − | − | − |
| D-arabitol | − | − | − |
| L-arabitol | − | − | − |
| Gluconate | − | − | − |
| 2-ceto-gluconate | − | − | − |
| 5-ceto-gluconate | − | − | − |

+ = Positive Reaction
− = Negative Reaction
+/− = Ambiguous Reaction (distinguishable from negative control)

TABLE 2

| Common Name | Latin Name |
|---|---|
| Western Corn Rootworm | *Diabrotica virgifera virgifera* |
| Southern Corn Rootworm | *Diabrotica undecimpunctata howardi* |
| Northern Corn Rootworm | *Diabrotica barberi* |
| Mexican Corn Rootworm | *Diabrotica virgifera zea* |
| Banded Cucumber Beetle | *Diabrotica balteata* |
| Western Spotted Cucumber Beetle | *Diabrotica undecimpunctata undecimpunctata* |

TABLE 3

Selective insecticidal activity of *B. thuringiensis* strain JHCC 4279 in the control of Western Corn Rootworm (*Diabrotica virgifera virgifera*).

| | | *B. thuringiensis* STRAIN: | | | | | | NON-TREATMENT CONTROL | |
|---|---|---|---|---|---|---|---|---|---|
| | RATE | JHCC 4279 | | JHCC 4580 | | JHCC 4360 | | | |
| INSECT | (ppm) | 1 | 2 | 1 | 2 | 1 | 2 | 1 | 2 |
| WCRW | 4800 | 40 | 56 | 56 | 64 | 4 | 8 | 0 | 8 |
| CPB | 40 | 12 | 13 | 93 | 93 | 0 | 14 | 0 | 8 |
| ECB | 160 | 0 | — | 0 | — | — | — | 0 | — |
|  | 5 | — | — | — | — | 85 | — | 0 | — |
| FAW | 80 | 0 | 0 | 48 | 8 | 96 | 100 | 11 | 4 |
| CEW | 80 | 15 | 4 | 0 | 12 | 100 | 100 | 1 | 4 |

Results are presented as % mortality. ppm = parts per million: — = not tested
WCRW = Western Corn Rootworm; these tests were read at 5 days after treatment
CPB = Colorado Potato Beetle; these tests were read at 3 days after treatment
ECB = European Corn Borer; these tests were read at 6 days after treatment
FAW = Fall Army Worm; these tests were read at 6 days after treatment
CEW = Corn Ear Worm; these tests were read at 5 or 6 days after treatment
1 and 2 = separate tests on the same treatment preparation.
JHCC 4360 is a lepidopteran-active subsp. *kurstaki* strain.
JHCC 4580 is a coleopteran-active subsp. *tenebrionis* - like strain.

TABLE 4

Efficacy of *B. turingiensis* strain JHCC 4279 in the control of two *Diabrotica spp.* over a treatment rate range.

| | WESTERN CORN ROOTWORM *B. thuringiensis* STRAIN: | | | | SOUTHERN CORN ROOTWORM *B. thuringiensis* STRAIN: | | | |
|---|---|---|---|---|---|---|---|---|
| RATE | JHCC 4279 | | JHCC 4580 | | JHCC 4279 | | JHCC 4580 | |
| (ppm) | 1 | 2 | 1 | 2 | 1 | 2 | 1 | 2 |
| 7500 | 61 | 76 | 60 | 80 | 40 | — | 46 | — |
| 4800 | 40 | 56 | 56 | 64 | 24 | — | 32 | — |
| 3072 | 12 | 20 | 24 | 44 | 20 | — | 16 | — |
| 1966 | 0 | 20 | 44 | 52 | 8 | — | 20 | — |

Non-treatment control mortalities:
Western Corn Rootworm 1 = 0% 2 = 8%
Southern Corn Rootworm 1 = 8%
Results are presented as % mortality at 5 days after treatment.
ppm = parts per million: — = not tested
1 and 2 = separate tests on the same treatment preparation

TABLE 5

Efficacy of *B. thuringiensis* strain JHCC 4279 in the control of two *Diabrotica spp.* 1 cup tests.

| | WESTERN CORN ROOTWORM TEST NUMBER: | | | | SOUTHERN CORN ROOTWORM TEST NUMBER: | | | |
|---|---|---|---|---|---|---|---|---|
| STRAIN JHCC | 1 | 2 | 3 | 4 | 1 | 2 | 3 | 4 |
| 4279 | 40 | 80 | 80 | 100 | 20 | 80 | 20 | 40 |
| 4580 | 80 | 80 | 80 | 80 | 60 | 20 | 60 | 60 |
| 4360 | 0 | 20 | 40 | 20 | 20 | 0 | 0 | 40 |
| CONTROL | 0 | 0 | 0 | 20 | 0 | 0 | 0 | 20 |

Results are presented as % mortality at 5 days after treatment at a treatment concentration of 4800 parts per million.

TABLE 6

Efficacy of *B. thuringiensis* strains JHCC 4279 and JHCC 4580 and the equivalence between separate preparations in the control of Western Corn Rootworm

| | *B. thuringiensis* STRAIN: | | | NON-TREATMENT CONTROL |
|---|---|---|---|---|
| PREP NO. | JHCC 4279 | JHCC 4580 | JHCC 4360 | |
| 1 | 57 | 56 | 20 | 4 |
| 2 | 44 | 88 | 20 | 4 |
| 3 | 56 | 68 | 8 | 8 |
| 4 | 80 | 56 | 4 | 8 |

Results are presented as % mortality at a treatment concentration of 4800 parts per million at 5 days after treatment.

TABLE 7

Specificity of insecticidal properties of *B. thuringiensis* strains over four separate preparations as tested on lepidopteran larvae.

| | CORN EARWORM TEST *B. thuringiensis* STRAIN: | | | FALL ARMY WORM TEST *B. thuringiensis* STRAIN: | | |
|---|---|---|---|---|---|---|
| PREP NO. | JHCC 4279 | JHCC 4580 | JHCC 4360 | JHCC 4279 | JHCC 4580 | JHCC 4360 |
| 1 | 0 | 8 | 100 | 4 | 0 | 84 |
| 2 | 0 | 0 | 100 | 4 | 0 | 80 |
| 3 | 0 | 0 | 100 | 4 | 0 | 88 |
| 4 | 0 | 4 | 100 | 0 | 8 | 100 |

Non-treatment control mortalities:
Corn Earworm test = 2%; Fall Army Worm test 3%

Results are presented as % mortality at 6 days after treatment at a treatment concentration of 80 parts per million.

TABLE 8

Insecticidal activity of partially-purified protein fractions from B. thuringiensis strain 4279 in the control of Western Corn Rootworm Diabrotica virgifera virgifera.

| | | | | % MORTALITY AT 5 DAYS | |
| --- | --- | --- | --- | --- | --- |
| | Hydroxylapatite-purified | | | STARTING MATERIAL | NON-TREAT- |
| Prep | Sample | Rate (ppm) | SAMPLE | AT 4800 PPM | MENT CONTROL |
| 5 | 5 A10 PART-PURE | 400 | 86 | 80 | 4 |
| | 5 B10 PART-PURE | 400 | 92 | 60 | 8 |
| | 5 CAPS EXTRACT | 500 | 42 | 60 | 8 |
| 6 | 5 A10 PART-PURE | 400 | 82 | 80 | 24 |
| | 6 B10 PART-PURE | 300 | 95 | 64 | 2 |
| | 6 CAPS EXTRACT* | 500 | 24* | 46* | 6* |

*Average of Two Tests.
ppm = parts per million.
Preps 5 and 6 represent separate experiments.
PART-PURE = Partially-purified samples containing 6-8 different proteins.
CAPS EXTRACT = Sonicated, CAPS-extracted material dialyzed into 10 mM Tris pH8.
STARTING MATERIAL = lyophilized fermentation product tested as described.
A10 = Hydroxylapatite-purified samples originally eluted from the Mono-Q column 0-100 mM NaCl.
B10 = Hydroxylapatite-purified samples originally eluted from the Mono-Q column in 100-200 mM NaCl.

We claim:

1. A biologically pure culture of *Bacillus thuringiensis* strain JH 4279, NCIB 40252.